United States Patent
Rafiee et al.

(10) Patent No.: US 10,154,902 B2
(45) Date of Patent: Dec. 18, 2018

(54) INFUNDIBULAR REDUCER DEVICE DELIVERY SYSTEM AND RELATED METHODS

(71) Applicant: Medtronic Vascular, Inc., Santa Rosa, CA (US)

(72) Inventors: Nasser Rafiee, Andover, MA (US); Morgan House, Newfields, NH (US); Nareak Douk, Lowell, MA (US); Philipp Bonhoeffer, London (GB)

(73) Assignee: Medtronic Vascular, Inc., Santa Rosa, CA (US)

( * ) Notice: Subject to any disclaimer, the term of this patent is extended or adjusted under 35 U.S.C. 154(b) by 28 days.

(21) Appl. No.: 15/152,593

(22) Filed: May 12, 2016

(65) Prior Publication Data
US 2016/0250023 A1     Sep. 1, 2016

Related U.S. Application Data

(62) Division of application No. 12/358,388, filed on Jan. 23, 2009, now Pat. No. 9,364,324.
(Continued)

(51) Int. Cl.
*A61F 2/24* (2006.01)
*A61M 5/00* (2006.01)
(Continued)

(52) U.S. Cl.
CPC .......... *A61F 2/2427* (2013.01); *A61F 2/2436* (2013.01); *A61M 5/007* (2013.01); *A61M 25/0043* (2013.01); *A61F 2/2418* (2013.01); *A61F 2002/9522* (2013.01); *A61F 2250/0039* (2013.01); *A61M 2025/0057* (2013.01)

(58) Field of Classification Search
CPC ........ A61F 2/95; A61F 2/2427; A61F 2/2436; A61F 2/2439; A61F 2002/9505; A61F 2002/9511
See application file for complete search history.

(56) References Cited

U.S. PATENT DOCUMENTS

| 5,234,437 A | 8/1993 | Sepetka |
| 5,480,424 A | 1/1996 | Cox |

(Continued)

FOREIGN PATENT DOCUMENTS

| WO | 2004/019825 A1 | 3/2004 |
| WO | WO2004/110521 | 12/2004 |

(Continued)

OTHER PUBLICATIONS

Bonhoeffer et al., "Percutaneous Insertion of the Pulmonary Valve" Journal of the American College of cardiology 2002; 39: 1664-1669.
(Continued)

*Primary Examiner* — Alexander Orkin
(74) *Attorney, Agent, or Firm* — Medler Ferro Woodhouse & Mills PLLC (57) ABSTRACT

Described is a delivery system for minimally invasive delivery of a self-expandable stent to a body lumen, and particularly delivery of a prosthetic valve to the right ventricular outflow tract. Also described is a method of loading a stent onto such a delivery system, and a method of delivering a self-expandable stent to a desired anatomic site.

9 Claims, 11 Drawing Sheets

Related U.S. Application Data (60) Provisional application No. 61/023,330, filed on Jan. 24, 2008.

(51) Int. Cl.
*A61M 25/00* (2006.01)
*A61F 2/95* (2013.01)

(56) References Cited

U.S. PATENT DOCUMENTS

| | | |
|---|---|---|
| 5,643,278 A | 7/1997 | Wijay |
| 5,702,418 A | 12/1997 | Ravenscroft |
| 5,713,948 A | 2/1998 | Uflacker |
| 5,749,920 A * | 5/1998 | Quiachon ............. A61B 17/11 606/195 |
| 5,797,952 A | 8/1998 | Klein |
| 6,395,017 B1 | 5/2002 | Dwyer et al. |
| 6,607,551 B1 | 8/2003 | Sullivan et al. |
| 6,719,789 B2 | 4/2004 | Cox |
| 7,942,924 B1 | 5/2011 | Perez et al. |
| 2003/0199963 A1 | 10/2003 | Tower et al. |
| 2003/0199971 A1 | 10/2003 | Tower et al. |
| 2004/0078071 A1 | 4/2004 | Escamilla et al. |
| 2004/0147939 A1 | 7/2004 | Rabkin et al. |
| 2004/0193209 A1 | 9/2004 | Pavcnik et al. |
| 2005/0137693 A1 | 6/2005 | Haug et al. |
| 2005/0137701 A1 | 6/2005 | Salahieh et al. |
| 2006/0111771 A1 | 5/2006 | Ton et al. |
| 2006/0155357 A1 | 7/2006 | Melsheimer |
| 2006/0259123 A1 | 11/2006 | Dorn |
| 2007/0100414 A1 | 5/2007 | Licata et al. |
| 2007/0100415 A1 | 5/2007 | Licata et al. |
| 2008/0140178 A1* | 6/2008 | Rasmussen ............... A61F 2/95 623/1.11 |
| 2008/0183272 A1 | 7/2008 | Wood et al. |
| 2010/0049313 A1* | 2/2010 | Alon ..................... A61F 2/2418 623/2.11 |

FOREIGN PATENT DOCUMENTS

| | | |
|---|---|---|
| WO | 2006/076890 A1 | 7/2006 |
| WO | 2007/021708 A1 | 2/2007 |
| WO | 2008/138584 A1 | 11/2008 |

OTHER PUBLICATIONS

Bonhoeffer et al., "Transcatheter Replacement of a Bovine Valve in Pulmonary Position" Circulation 2000: 102:813-816.

Khambadkone et al., "Percutaneous Pulmonary Valve Implantation in Humans" Circulation 1189-1197; Aug. 23, 2005.

* cited by examiner

INFUNDIBULAR REDUCER DEVICE DELIVERY SYSTEM AND RELATED METHODS

CROSS-REFERENCE TO RELATED APPLICATION

The present application is a Division of and claims priority to U.S. patent application Ser. No. 12/358,388, filed Jan. 23, 2009, now allowed; which claims priority to U.S. Provisional Application No. 61/023,330, filed Jan. 24, 2008, the entire contents of which are incorporated herein by reference in their entirety.

TECHNICAL FIELD

This invention relates generally to the treatment of cardiac valve disease using prosthetic valves, and more particularly to replacement of malfunctioning pulmonary valves using infundibular reducer devices.

BACKGROUND OF THE INVENTION

Natural heart valves, such as aortic valves, mitral valves, pulmonary valves and tricuspid valves, often become damaged by disease in such a manner that they fail to maintain blood flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement generally has been accomplished by major open heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, co-existing infection, or other physical limitations.

Recently, there has been increasing interest in minimally invasive and percutaneous replacement of cardiac valves, typically by way of catheterization. In minimally invasive procedures, a catheter is used to insert a mechanical or bioprosthetic valve in a lumen of a blood vessel via percutaneous entry through a distal blood vessel. Typically, such percutaneous prosthetic valve devices comprise an expandable stent segment, a stent anchoring segment and a flow-regulation segment, such as a ball valve or a biological valve. The expandable stent portion is generally expanded using a balloon that is part of a transcatheter delivery system.

In the specific context of pulmonary valve replacement, U.S. Patent Application Publication Nos. 2003/0199971 A1 and 2003/0199963 A1, both filed by Tower, et al. and incorporated herein by reference, describe replacing a pulmonary valve with a venous valvular replacement. The replacement pulmonary valve is mounted on a balloon catheter and delivered percutaneously via the vascular system to the location of the failed pulmonary valve and expanded by the balloon to compress the native valve leaflets against the right ventricular outflow tract, anchoring and sealing the replacement valve. As described in the articles: *Percutaneous Insertion of the Pulmonary Valve*, Bonhoeffer, et al., Journal of the American College of Cardiology 2002; 39: 1664-1669 and *Transcatheter Replacement of a Bovine Valve in Pulmonary Position*, Bonhoeffer, et al., Circulation 2000; 102: 813-816, both incorporated herein by reference in their entireties, the replacement pulmonary valve may be implanted to replace native pulmonary valves or prosthetic pulmonary valves located in valved conduits. Surgical procedures for percutaneous pulmonary valve implantation are described in Khambadkone et al., *Percutaneous Pulmonary Valve Implantation in Humans*, Circulation, 1189-1197 (Aug. 23, 2005).

Pulmonary valve replacement using venous valves is not available to all who might benefit from it due to the relatively narrow size range of available valved segments of veins, for example, with typical sizes available only up to a diameter of about 22 mm. The same limited availability of sizes also applied to pericardial valves.

Unfortunately, many patients requiring pulmonary valve replacement are adults and children who have right ventricular outflow tracts that are larger than 22 mm in diameter. This could have resulted, for example, from having previously undergone transannular patch repair of tetralogy of Fallot during infancy. There are other causes, however, for an enlarged right ventricular outflow tract. Thus, venous valvular replacements with a limit of 22 mm diameters, cannot typically be securely implanted within these patients. The same generally applies for pericardial heart valve replacements.

Thus, there is a continuing need to improve upon the devices available for heart valve replacement, in particular those including venous valve replacements or pericardial heart valves, and even more particularly those that may be placed in patients with right ventricular outflow tracts larger than 22 mm in diameter. In addition, there is a continuing need for improved transcatheter delivery systems and methods of implanting medical devices, and particularly systems related to heart valve replacement.

SUMMARY OF THE INVENTION

The present invention provides a delivery system and a method for replacing a malfunctioning heart valve, and in particular, a pulmonary heart valve, by delivering a prosthetic valve through percutaneous transcatheter implantation to a valved anatomic site within the heart. Specifically, the delivery system and method may be used to deliver an infundibular reducer device including a pericardial heart valve, a valved segment of bovine jugular vein or another collapsible valve to the right ventricular outflow tract. However, the delivery system and methods are not limited to delivery of infundibular reducers, and may be used to deliver any suitable medical device to any applicable anatomic site.

A benefit of the invention is that it allows for delivery of a medical device through a catheter to a desired anatomic site and expansion of the medical device without the need for a balloon for deployment of the device. A system that does not require a balloon during deployment or expansion does not cause potential occlusion of blood flow through a portion of the heart for a period of time. Eliminating the balloon also reduces the bulkiness of the delivery system, which makes the delivery system easier to insert and remove intraluminally.

Another benefit of the invention is that the medical device being delivered may be collapsed and repositioned after partial deployment or expansion of the device. This is beneficial if it is determined during certain early stages of delivery that the replacement valve is not being placed correctly. The replacement valve may then be easily re-compressed and moved to the correct location.

A first aspect of the invention is a delivery system for delivery of a device to a body lumen. The device may comprise: a proximal end and a distal end, a central lumen there through, and a plurality of attachment members located at or near the proximal end. One embodiment of the system comprises: an elongated inner catheter having a proximal end and a tapered, distal end for insertion into a body lumen; an elongated holding catheter having a proximal end, a distal end, a center lumen passing there through to slidably maintain the inner catheter and a coil on the distal end for attachment to the plurality of attachment members on the device; and an elongated outer sheath having a proximal and a distal end and a center lumen passing there through to slidably and rotatably maintain the holding catheter, to collapse the device as the holding catheter is slid proximally there through, and to hold the device in a collapsed configuration for delivery to a body lumen. The outer sheath may further comprise a funnel removably connected to the distal end for collapsing the device as the holding catheter is slid proximally there through. The delivery system may further comprise: a loading rail that comprises a substantially circular shaped tube with two free ends, wherein the loading rail is attachable to the plurality of attachment members on the device and comprises a first end that is removably attachable to the coil to provide a continuous path for the attachment members of the device to be transferred from the loading rail to the coil. The delivery system may further comprise the device. The device may further comprise a replacement valve that is attached within the central lumen of the device. The plurality of attachment members may comprise loops. The delivery system may further comprise dye injection ports in the outer sheath through which dye may flow from the system to a body lumen. The device may be self-expandable. The system may further comprise at least one purging vent at or near the distal end of the inner catheter through which fluid injected into the inner catheter is able to escape the system.

A second aspect of the invention is a method of loading a device onto a delivery system. One embodiment of the method comprises the steps of: receiving a self-expanding device having a proximal end and a distal end, a central lumen there through, and a plurality of attachment members located at or near the proximal end; receiving a delivery system comprising a loading rail having two free ends, an elongated inner catheter having a proximal end and a tapered distal end, an elongated holding catheter having a proximal end and a distal end comprising a coil for attachment to the device and a center lumen passing there through to slidably maintain the inner catheter and the coil, and an elongated outer sheath having a proximal and a distal end and a center lumen passing there through; extending the inner catheter through the lumen of the holding catheter and extending both the inner catheter and holding catheter through the lumen of the outer sheath; threading the plurality of attachment members onto the loading rail; connecting one free end of the loading rail to the coil on the holding catheter; advancing the plurality of attachment members along the loading rail and onto the coil, wherein the advancing procedure partially collapses the device; removing the loading rail from the coil after all of the attachment members are transferred to the coil; collapsing the device in the outer sheath by sliding outer sheath over the stent; and enclosing the collapsed device by retracting the inner catheter proximally and pulling the distal tapered end into the distal end of the outer sheath. The plurality of attachment members may comprise loops. The device may be a prosthetic valve that further comprises a replacement valve that is attached to the device within the central lumen.

A third aspect of the present invention is a method of delivering a self-expandable device to a desired anatomic site. The method may comprise the steps of: receiving a delivery system comprising: a device having a proximal end and a distal end and a central lumen there through, and a plurality of attachment members at the proximal end; an elongated inner catheter having a proximal end and a tapered, distal end for insertion into a body lumen; an elongated holding catheter having a proximal end and a distal end and a center lumen that slidably maintains the inner catheter passing there through, and a coil on the distal end attached to the plurality of attachment members on the device; and an elongated outer sheath having a proximal and a distal end and a center lumen passing there through slidably and rotatably maintaining the holding catheter and inner catheter, the distal, tapered end of the inner catheter maintained in the distal end of the outer sheath, and holding and enclosing the device in a collapsed configuration for delivery to a desired anatomic site; advancing the delivery system intraluminally toward the anatomic site; upon reaching the anatomic site, retracting the outer sheath to allow the stent to partially expand; rotating the holding catheter in order to release the attachment members of the device from the coil and allowing the device to expand, thereby releasing the device from the delivery system; and removing the delivery system from the anatomic site. The device may further comprise a replacement valve connected to the device in the central lumen of the device. The plurality of attachment members may comprise loops. The delivery system may further comprise dye injection ports through which dye may flow from the system to the anatomic site, and the method may further comprise the step of delivering dye through the dye injection ports. The dye may be delivered under visualization. Visualization may be achieved by using a procedure chosen from the group consisting of fluoroscopy, echocardiography, intravascular ultrasound, angioscopy and real-time magnetic resonance imaging.

BRIEF DESCRIPTION OF THE DRAWINGS

The invention will be further explained with reference to the appended Figures, wherein like structure is referred to by like numerals throughout the several views, and wherein.

DETAILED DESCRIPTION

With reference to the accompanying figures, wherein like components are labeled with like numerals throughout the figures, an illustrative delivery system and method of the delivery of infundibular reducer devices is disclosed, taught and suggested by the multiple embodiments.

The embodiments of the invention described below are not intended to be exhaustive or to limit the invention to the precise forms disclosed in the following detailed description. Rather the embodiments are chosen and described so that others skilled in the art may appreciate and understand the principles and practices of the invention.

The principles of the invention may be practiced in any instance in which it is desired to deliver a medical device intraluminally to a desired anatomic site. For the purpose of discussion, the invention will generally be described in the context in which the medical device being loaded and delivered is a prosthetic valve, and specifically an infundibular reducer device. This illustrative context shows how corresponding embodiments of the invention are particularly useful for delivering an infundibular reducer, including a pericardial heart valve, a valved segment of bovine jugular vein, or some other collapsible valve, to the right ventricular outflow tract. However, other uses of the invention, such as to deliver different medical devices to different locations in the body, are contemplated and are not limited to those discussed in the application.

Referring now to the FIGS. 1-10, wherein components are labeled with like numerals throughout the several Figures, an embodiment of a first aspect of the invention is shown, which is a delivery system 100. Steps of the related methods are also shown in the FIGS. 1-10. The steps shown involve loading an infundibular reducer device 500 on the delivery system 100 and delivering the device 500.

Figure 1:
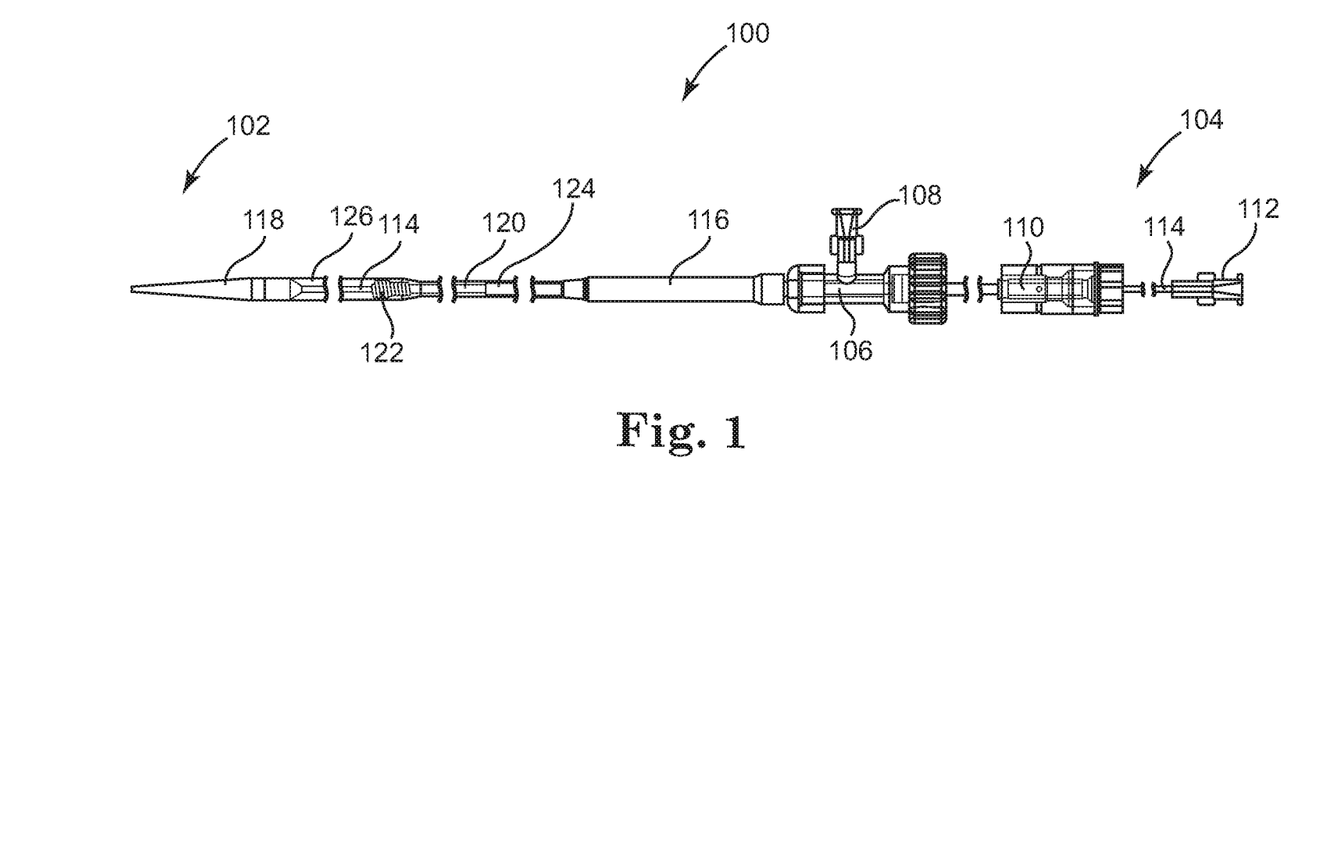
FIG. 1 illustrates a perspective view of a delivery system in accordance with the present invention.

The delivery system 100 is illustrated in FIG. 1. The system 100 includes a distal end generally designated by the reference numeral 102 and a proximal end generally designated by the reference number 104. The distal end 102 is preferably used to load and deliver an infundibular device, for example, which will be described in detail below. The proximal end 104, which is not shown in subsequent figures, preferably includes components such as those found in other catheter delivery systems.

The components of the proximal end 104 of the delivery system 100 may preferably include those shown in FIG. 1, although additional and/or alternative components are also contemplated. FIG. 1 includes a first rotating homeostasis valve 106, a side access port 108, a second rotating homeostasis valve 110, and a guidewire lumen inlet 112. The first rotating homeostasis valve 106 is most preferably comprised of latex and grips or forms a fluid seal around the delivery system 100 to prevent blood or other fluid from leaking out of the delivery device at the proximal end or entry site into a patient. The side access port 108 is provided as a means for injecting contrast media or saline, for example, into the delivery system 100. The second rotating homeostasis valve 110 is like first valve 106 in that it preferably prevents blood or other fluid from leaking back through the system 100. In addition, the second valve 110 is preferably configured to allow wires, devices and fluid to pass through. Furthermore, second valve 110 also preferably controls the components of the distal end (as described below) by rotation of a portion of the valve 110. The first and second valves 106, 110 are preferably compatible with normal catheter-laboratory components. Such first and second valves 106, 110 are preferably similar to those generally known in catheter systems.

The delivery system 100 is preferably designed for use in the femoral artery. The useable length of the system 100 from the distal end 118 to an outer sleeve 116 is preferably about 100 to 105 centimeters, although other lengths are also contemplated. The proximal end 104 of the device preferably extends outside of the patient in the groin area, while the distal end 102 is preferably delivered intravascularly to an area at or near a pulmonary valve inside the body. Other uses for the system 100 in other areas of the body, however, are also contemplated.

The delivery system 100 is configured to allow for coaxial use to pass items such as guidewires, devices, contrast media and other catheters through the system 100. The delivery system 100 preferably includes an inner catheter 114 that includes a guidewire lumen, and is connected to a guidewire lumen inlet 112 at the proximal end of the inner catheter 114. The inner catheter 114 preferably extends along the entire length of the system 100 in order to allow a guidewire to pass from the proximal end 104 and out through the distal end 102. Inner catheter 114 may be slid or moved through other components of the system 100 by moving the guidewire lumen inlet 112 to which it is attached. The system 100 may include a guidewire, which may be, for example a 0.089 cm extra stiff guidewire as manufactured by Amplatzer, Golden Valley, Minn., U.S.A. The guidewire can be used to guide the delivery system 100 to its desired implant location, and can extend through the inner catheter 114. Other guidewires are also contemplated, however.

The outer sleeve 116 preferably is located between the proximal end 104 and the distal end 102 of the system 100. The purpose of the sleeve 116 is to keep blood from leaking back around the delivery system 100. The components of the proximal end 104 of the system 100 are exemplary. Other alternative or additional components of the proximal end 104 of the delivery system 100 are also contemplated by the invention.

FIG. 1 shows the distal end 102 of the system 100 in an assembled configuration, without an infundibular reducer device attached or loaded. Attached to the inner catheter 114 is a tapered tip 118, which serves to ease the passage of the delivery system 100 through the vasculature. Also shown is a device holding catheter 120 upon which a prosthetic valve, or other medical device to be delivered, is attached or held during delivery. The holding catheter 120 includes a centrally located lumen surrounding the inner catheter 114. The holding catheter 120 is able to slide relative to the inner catheter 114, and its movement is controlled by the second valve 110 at the proximal end 104 of the system 100. Preferably, a portion of second valve 110 is rotated or otherwise manipulated in order to rotates holding catheter 120 or moves the holding catheter 120 proximally and distally as desired.

A coil 122 is preferably attached to the distal end of the holding catheter 120. Thus, movement of the holding catheter 120, as controlled by second valve 110, controls movement or rotation of coil 122. The purpose of the coil 122 is to provide a means for loading a device 500 onto the system 100, holding the device 500 on the system 100 during delivery, and releasing the device 500 from the system 100. The speed that the device 500 is released from the system 100 is controlled by the rate of rotation of the coil 122, therefore preventing uncontrolled release of the device 500 in a manner known in the art as "jumping." Surrounding the holding catheter 120 is a reinforcement layer 124, which is attached or otherwise bonded to the holding catheter 120 and serves to reinforce the catheter 120.

The distal end 102 of the delivery system 100 also includes the outer sheath 126 that is preferably made of a low friction and flexible material, such as polytetrafluoroethylene (PTFE), polyurethane, silicone, or polyethylene. The outer sheath 126 is sized and shaped in order to house other distal end 102 components of the delivery system 100.

FIGS. 2-10 show the delivery system 100 of the invention, and show one exemplary medical device that can be delivered by the delivery system 100. The exemplary medical device 500 shown is a prosthetic valve, and in particular an infundibular reducer device 500, but is only one example of a medical device that may be delivered by the delivery system 100.

Figure 2:
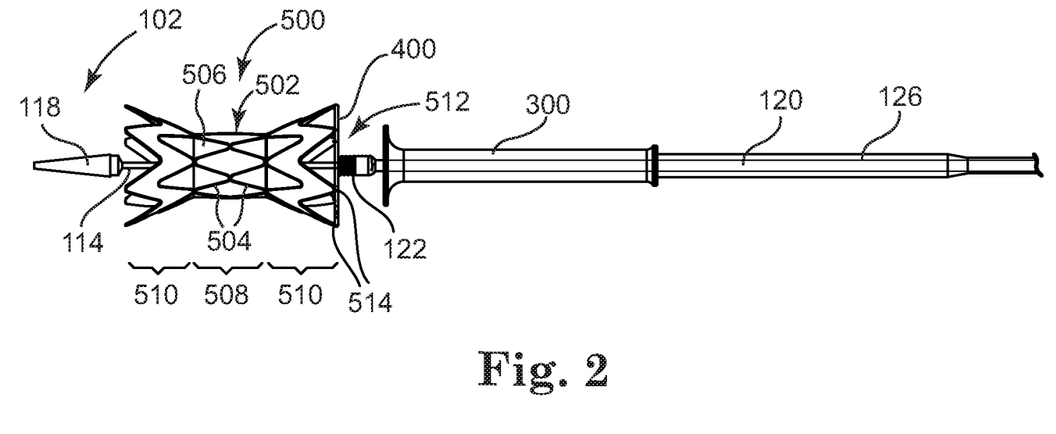
FIG. 2 illustrates a perspective view of a delivery system and a prosthetic valve in accordance with the present invention prior to loading the prosthetic valve on the remainder of the system.

FIG. 2 illustrates the exemplary infundibular reducer device 500 surrounding the distal end 102 of the system 100, but not yet attached to or loaded onto the system 100. Generally, the device 500 comprises a self-expandable stent portion 502 that may be expanded from a first reduced diameter to a second enlarged diameter. The device 500 is compressible to be inserted via catheter and expandable to fit a desired body lumen, such as the right ventricular outflow tract, for example. In order to be self-expandable, the self-expandable stent 502 is at least partially formed into its desired configuration using a material or materials and a form that may be compressed and that will regain the desired configuration upon release from compression. The stent portion 502 is preferably formed into a desired shape and made from a framework that comprises a wire or plurality of wires 504 made of a shape-memory material (e.g., NITINOL™) and preferably one or more pieces of fabric 506 (i.e., cloth, material, etc.) to which the wire or wires 504 are attached.

The wires 504 of the stent 502 are shaped and aligned such that when the wires 504 are aligned generally coaxially, a central lumen runs along the length of the stent 502. The wires 504 preferably include a series of sinusoidal bends around their circumference, which allow for the compression and expansion of the stent 502 with minimal force. The wires may be attached separately to the fabric 506. In addition or alternatively, the wires 504 may be attached to each other at some or all of their adjacent apices.

The stent 502, of the construction and configuration as herein described, preferably has good flexibility, dimensional stability, smooth surfaces, a low profile when collapsed, and an immunity to fatigue and corrosion. The length of the stent 502 can be varied by varying the number of wires 504 that are utilized, by varying the arrangement of wires and/or by varying other features of the wires and arrangement of wires. The working range of the stent 502 between its collapsed condition/configuration and its expanded condition can also be varied by the number of curves or bends in each wire. The stent 502 may be tailored for insertion into a particular body site to provide for the most effective implantation of the replacement valve which is attached to the stent 502.

The fabric 506 used for the stent 502 can be a polyester knit, for example, or may instead be ultra high molecular weight polyethylene (UHMWPE), cotton, or the like. The fabric 506 should be biocompatible and may include a number of different fabrics in different areas of the stent 502 and/or in layers, if desired.

The shape of the self-expandable stent 502 shown in the figures is one exemplary shape, and has a generally hourglass shape. Such an hourglass shape (with stent 502 in expanded configuration) includes a center 508 that is generally cylindrical in shape with a smaller diameter than ends 510. One advantage of the center 508 having a smaller diameter than the ends 510 is to allow at least a portion of the center 508 of the stent 502 to hold or retain a replacement valve (e.g., a pericardial heart valve or a valved segment of bovine jugular vein) in its central lumen (not seen in Figures), when such a replacement valve has a smaller diameter than the lumen in which the device 500 is to be placed. The larger diameter of the ends 510 allows the device 500 to be secured in place in a tubular organ, or a valved anatomic site, having a diameter larger than that of the replacement valve but smaller than the expanded diameter of the ends 510. The ends 510 are also shown to be flared, such that they increase in diameter from where the ends 510 extend from the center 508. The angle at which these ends 510 are flared from the center 508 can vary depending on the desired maximum diameter and desired length of the stent 502.

In the particular prosthetic valve 500 shown in the Figures, the ends 510 can be articulable with respect to the center 508 when the wires 504 used for the framework of the center 508 and ends 510 are not attached to each other. However, the wires 504 of the center 508 may be attached to the wires 504 of one or both ends 510. In this case, the center 508 and ends 510 can still be articulable relative to each other.

The replacement valve (not shown) preferably included in the prosthetic valve 500 is a preserved bovine jugular vein of the type described in the above-cited Bonhoeffer, et al. and Tower, et al. references. Other vessels or donor species may, however, alternatively be employed. Alternatively, other substantially tubular valve bodies may be the replacement valves of the invention. Such replacement valves may be formed from a variety of materials including biological materials and polymers. Biological material includes homograft, allograft or xenograft, with xenograft being common and well accepted and usually from bovine, ovine, swine or porcine pericardium, or a combination thereof. Polymers include expanded TEFLON™ polymers, high density polyethylene, polyurethane, and combinations thereof. Some examples of replacement valves used in the invention are described in U.S. Pat. Nos. 6,719,789 and 5,480,424, issued to Cox (which are incorporated herein by reference). The replacement valve is attached to (i.e., affixed to, held by, retained by, etc.) the stent 502, preferably, along its proximal and distal edges and is sutured or otherwise attached within the stent 502. As discussed above, the replacement valve is preferably positioned within the center 508 of the stent 502.

The prosthetic valve 500, or other medical device, that is part of the delivery system 100 of the invention preferably includes, on its proximal end 512, a plurality of attachment members (not visible on figures, but present on proximal-most extensions 514 of device 500 on the proximal end 512 of device 500), such as loops, for example, that allow the prosthetic valve 500 or medical device to be loaded onto (and unloaded from) the delivery system 100. In the exemplary prosthetic valve 500 in the Figures, there are a plurality of attachment loops (not visible) provided on the wires 504 at the proximal end 512 of the prosthetic valve 500. Such attachment loops may be formed from sutures, from the fabric used to form part of the stent 502, or other materials. The attachment loops may be made of UHMWPE thread, for one example, since this material advantageously has the properties of being durable and lubricous, as well as hydrophobic, which can help to minimize swelling or clotting due to contact with blood. However, other materials may be used that comprise some or all of these attachment loop properties.

Other attachment members besides loops are also contemplated by the invention. Such attachment members are preferably able to connect, fasten or attach the medical device or prosthetic valve 500 to the remainder of the delivery system 100 and allow for collapse of the medical device or prosthetic valve 500 for insertion into the body, and also are preferably able to be released from the remainder of the delivery system 100 in order to release the medical device or prosthetic valve 500 at a desired anatomic site.

The preferred delivery system 100 is illustrated in FIGS. 1-10, and is generally long and tubular permitting percutaneous delivery of the device 500 to a placement site. The proximal end 104 of the delivery system 100 preferably remains outside of the patient, and the distal end 102 is inserted into the patient. The proximal end 104 allows access to the interior of the delivery system 100 and includes means for remotely controlling the distal end 102 of the system 100, in particular relating to loading and delivery of such a device 500 on the system 100.

Referring to FIG. 2, the prosthetic valve 500 is prepared to be loaded onto the delivery system 100. The loading is preferably done outside the body prior to insertion of the delivery system 100 into a vein or other body lumen. The loading involves extending the distal portion 102 of the delivery system 100, and specifically the inner catheter 114 and tapered tip 118, through a central lumen of the valve or device 500. The proximal end 512 of the prosthetic valve 500, in order to be loaded using the described method, includes attachment loops (not visible) preferably on its proximal-most extensions 514. The loops are preferably made of suture material or other material, as described above, and function to provide a way to connect or attach the prosthetic valve 500 to the remainder of the delivery system 100.

Referring to FIG. 2, in order to load or attach the prosthetic valve 500 to the coil 122 of the delivery system 100, a loading rail 400 is inserted through the attachment loops (not shown) on the proximal-most extensions 514 of device 500.

Figure 3:
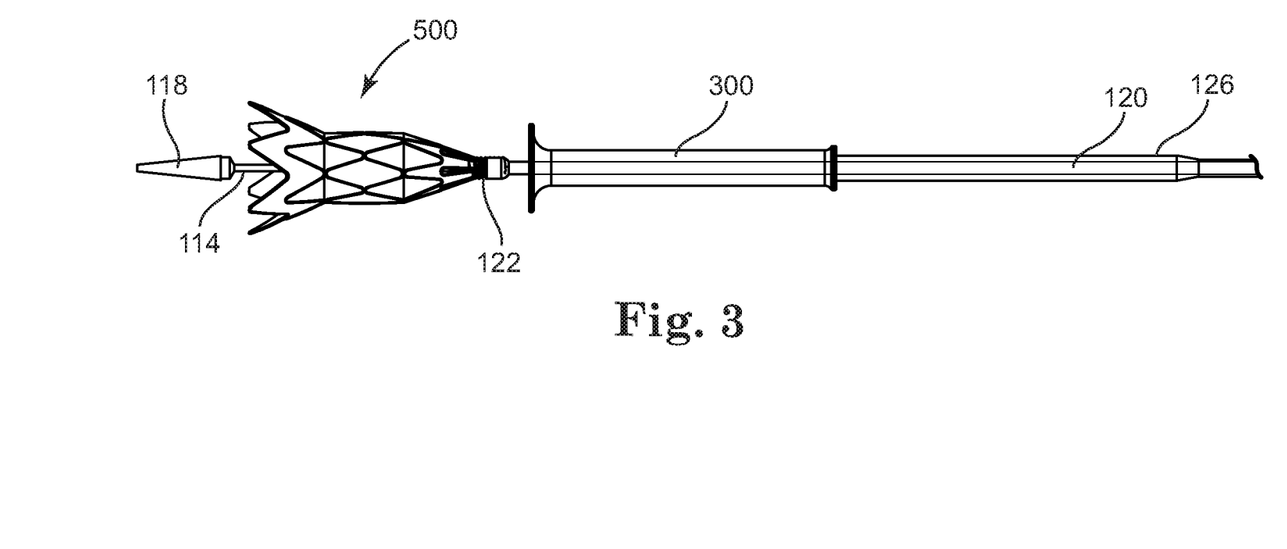
FIG. 3 illustrates a subsequent step in the loading method from the illustration in FIG. 2, in which the prosthetic valve is attached to a coil and is being collapsed from a proximal end so that it may be retracted into a loading funnel.

The loading rail 400 is preferably flexible plastic tubing or similar material that is threaded through the attachment loops. The loading rail 400 has two free ends. Both free ends of the loading rail 400 preferably have a central lumen, hollow area. One of the free ends of the loading rail is cut at an angle to allow ease of insertion into the attachment loops and the other end is square cut to allow that free end to be placed on or otherwise attached to the coil 122. For example, the loading rail 400 and coil 122 can be attached by a frictional fit (e.g., one of the loading rail 400 and coil 122 can slip over the other to connect the two components). Once the loading rail 400 is connected to the coil 122, the proximal-most extensions 514 that include the loops that are on the loading rail 400 are each manually pushed one-by-one along the loading rail 400, then onto the coil 122. As the extensions 514 are pushed along and onto the coil 122, the proximal end 512 of the device 500 is compressed or collapsed. Once all of the proximal-most extensions 514 are pushed off the loading rail 400 and are loaded onto the coil 122, the loading rail 400 is removed from the coil 122. FIG. 3 shows the proximal end 512 of the prosthetic valve 500 connected to the coil 122 as described, with the proximal end 512 of the valve 500 being compressed to closely match the diameter of the coil 122.

In order to further compress the device 500, and eventually enclose the device 500 for insertion into vasculature, a loading funnel 300 is used. The loading funnel 300 is shown in FIGS. 2 and 3. The loading funnel 300 is preferably loaded onto the system 100 from the proximal end 104 of the system 100 to a location as shown in FIGS. 2 and 3. The purpose of the loading funnel 300 is to gradually compress the prosthetic valve 500 for eventual enclosure in the system 100.

Figure 4:
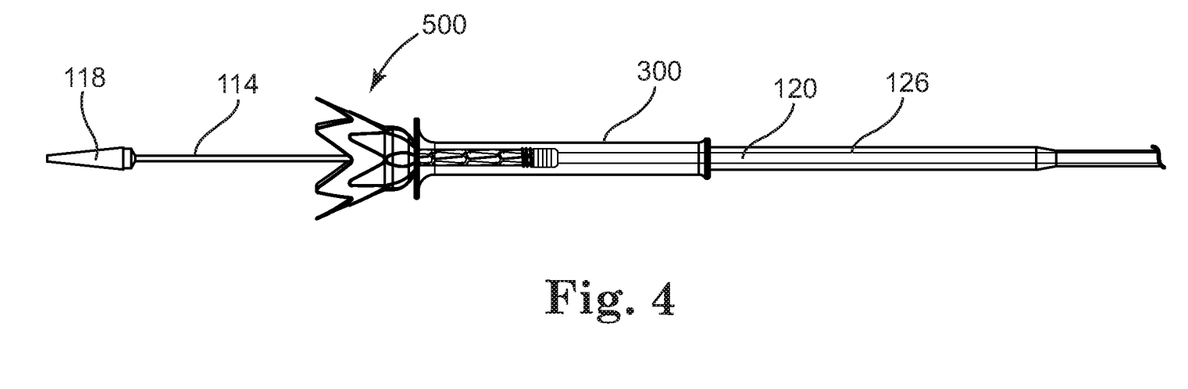
FIG. 4 illustrates a subsequent step in the loading method from the illustration in FIG. 3, in which the prosthetic valve is being collapsed and retracted into the loading funnel.

Once the device 500 is attached to coil 122, the holding catheter 120 may be retracted proximally, which pulls or moves the device 500 proximally as well. The loading funnel 300, then is held in place in order for the device 500 to be compressed in the loading funnel 300. FIG. 4 shows the device 500 partially compressed in the loading funnel 300. Alternatively, the loading funnel could be advanced proximally causing the device 500 to be compressed by advancement of the loading funnel 300.

Figure 5:
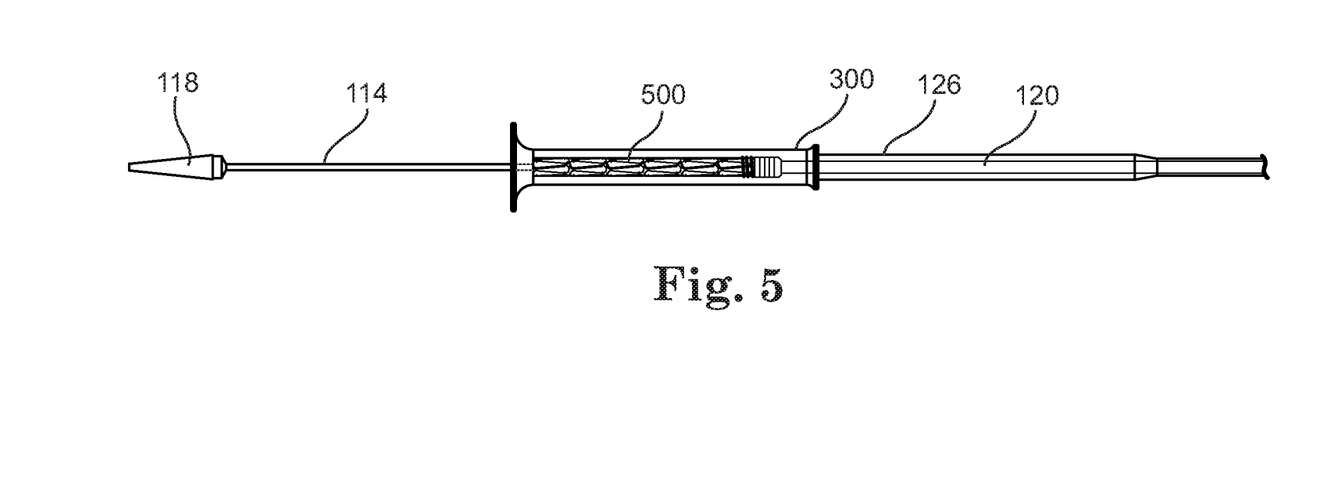
FIG. 5 illustrates a subsequent step in the loading method from the illustration in FIG. 4, in which the prosthetic valve is collapsed and retracted into the loading funnel.

FIG. 4 shows the loading funnel 300 surrounding and compressing a portion of the prosthetic valve 500. FIG. 5 then shows the next step in which the prosthetic valve 500 is completely enclosed within the loading funnel 300, with the inner catheter 114 and tapered tip 118 still extending out and through the distal end of the holding catheter 120.

Figure 6:
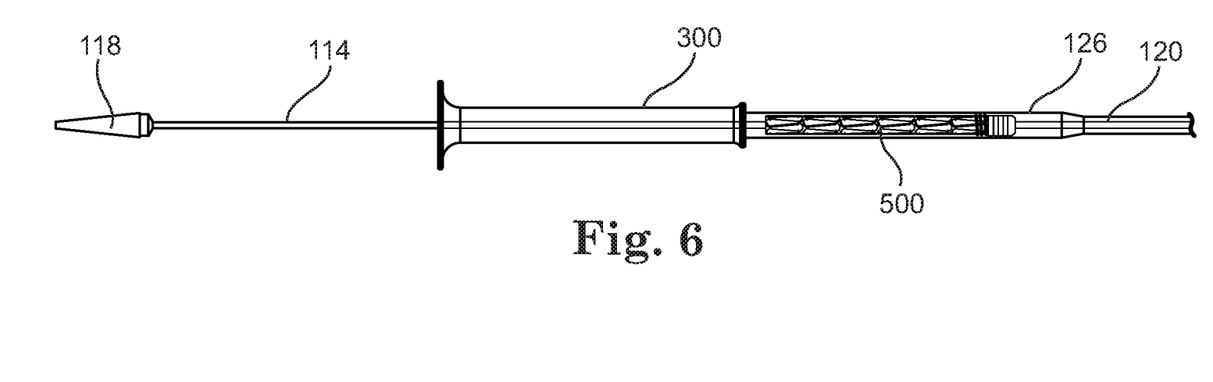
FIG. 6 illustrates a subsequent step in the loading method from the illustration in FIG. 5, in which the prosthetic valve is retracted into an outer sheath.

Next, FIG. 6 shows the collapsed prosthetic valve 500 even further retracted into the outer sheath 126. The device 500 is no longer inside the loading funnel 300. The outer sheath 126 then contains the collapsed prosthetic valve 500 in order to compress the prosthetic valve 100 to have a profile reduced enough to be inserted into a desired anatomic site, and to provide a smooth profile for insertion. The loading funnel 300 may then be removed from the remainder of the system 100.

Figure 7:
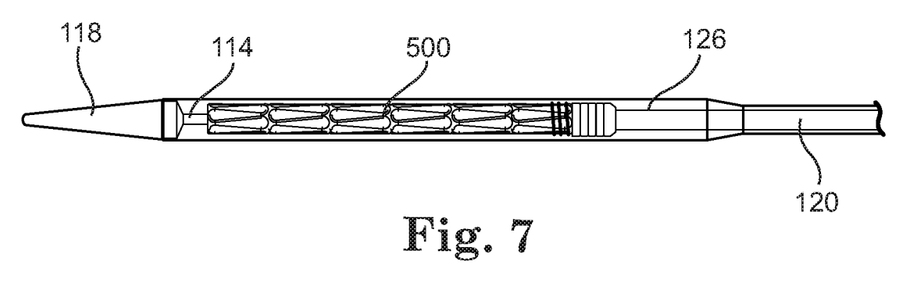
FIG. 7 illustrates a subsequent step in the loading method from the illustration in FIG. 6, in which the prosthetic valve is enclosed in the outer sheath in a collapsed configuration and is ready for intraluminal insertion or delivery to a desired anatomic site.
Figure 8:
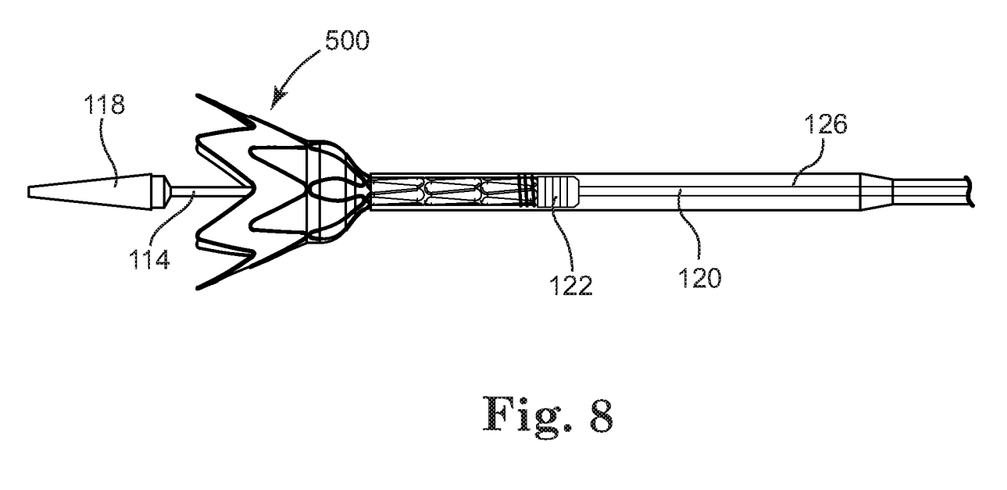
FIG. 8 illustrates a subsequent step from the loading method in FIG. 7, in the delivery of the prosthetic valve, in which the outer sheath is partially retracted and the prosthetic valve is partially expanded.

Once the prosthetic valve 500 is retained in its collapsed configuration in the outer sheath 126, the loading funnel 300 is preferably removed from the remainder of the delivery system 100 by sliding it toward the distal end 102 of the system 100. The inner catheter 114 is then retracted or pulled proximally towards the outer sheath 126 until the tip 118 fits into the distal end of the outer sheath 126, enclosing the prosthetic valve 500 in the outer sleeve for insertion into the body. The distal end of the resulting, loaded delivery system 100 with prosthetic valve 500 is shown in FIG. 7. FIG. 7 shows the distal end of the delivery system 100 as it can be inserted intraluminally to a desired anatomic site for delivery of the prosthetic valve 500.

Figure 9:
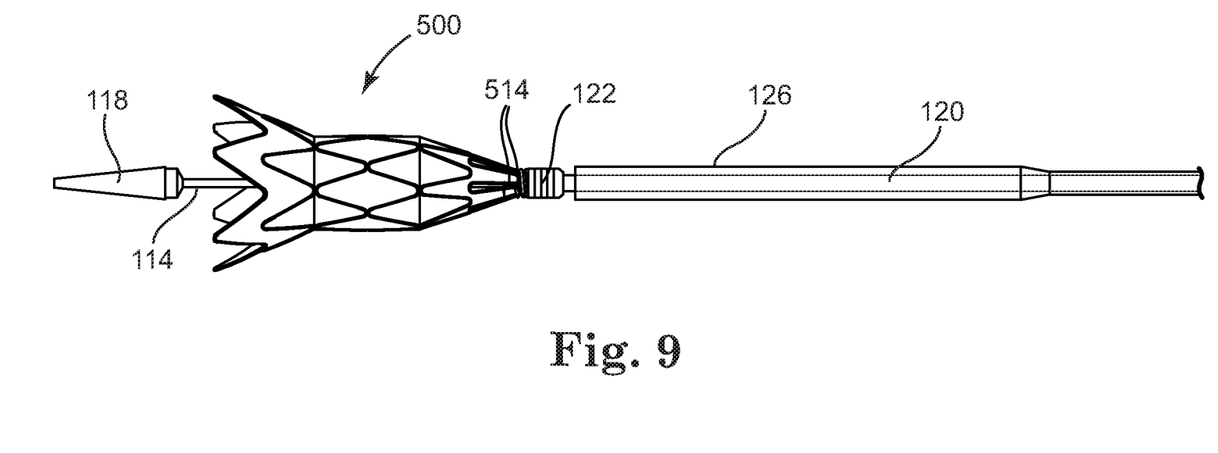
FIG. 9 illustrates a subsequent step in the delivery of the prosthetic heart valve from the illustration in FIG. 8, in which the outer sheath is retracted from the prosthetic valve and the prosthetic valve is partially expanded with the proximal end still attached to the coil.

In order to deploy or release the prosthetic valve 500 once it has been positioned at its desired location in the vasculature or in a heart valve annulus, for example, the outer sheath 126 is either retracted proximally, or the device 500 is pushed out the end of the outer sheath 126 by the holding catheter 120. As shown, in FIG. 8, the collapsed prosthetic valve 500 is begun to be released. In FIG. 9, the outer sheath 126 has been further retracted until the outer sheath 126 no longer surrounds the prosthetic valve 500, while the proximal-most extensions 514 (via loops that are not visible on this figure) are still attached to the coil 122. Until the proximal-most extensions 514 are released from the coil 122 by rotation of the knob at the distal end of the second valve 110, the delivery process is reversible. In other words, until the device 500 is free from the system 100, the prosthetic valve 500 may be retracted back into the outer sheath 126 and the delivery system 100 may be reassembled in order to move the delivery system 100 to another location.

Figure 10:
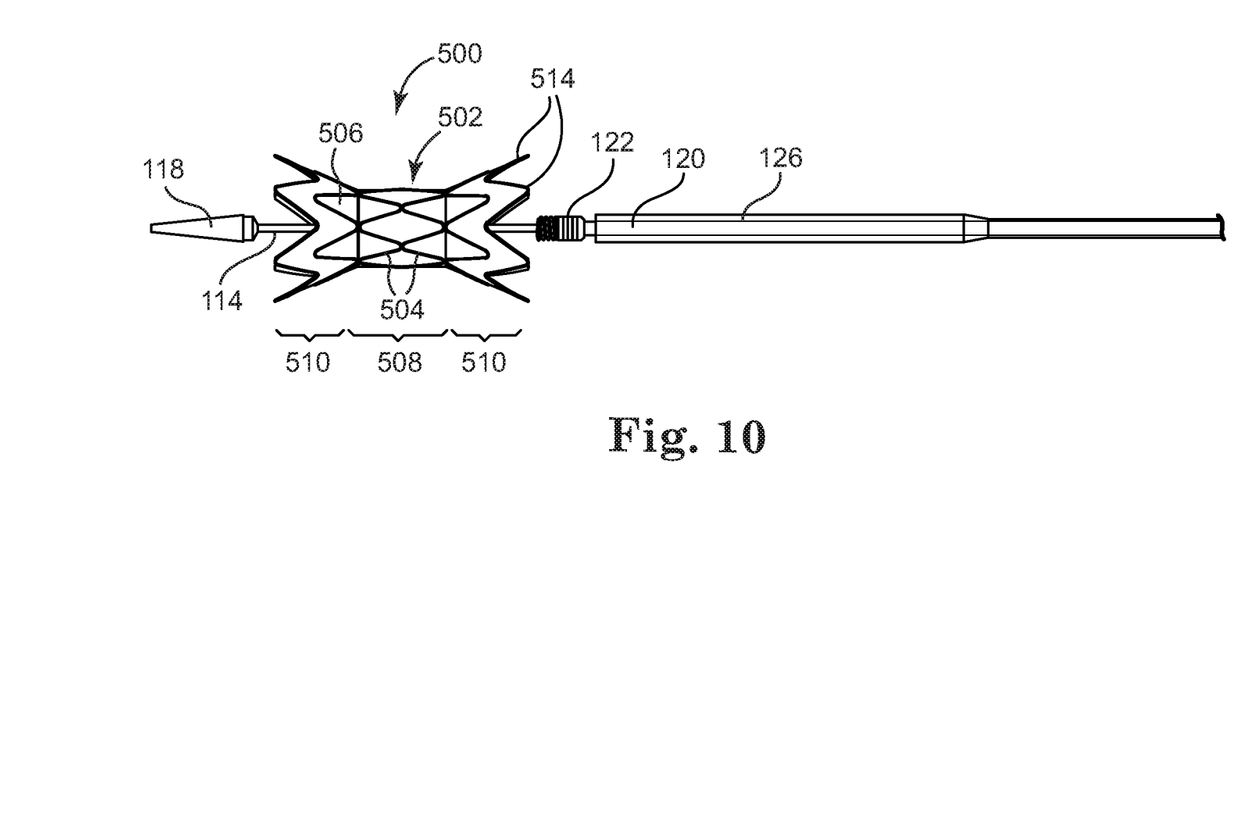
FIG. 10 illustrates a subsequent step in the delivery of the prosthetic valve from the illustration in FIG. 9, in which the prosthetic valve is released from the delivery system.

In order to release the device 500, the device 500 is released from within the outer sheath 126. Next, the loops on the proximal-most extensions 514 of the device 500 are released from the coil 122 by remotely rotating the holding catheter 120 from the proximal end of the delivery system 100 (at second valve 110) until all of the loops are free from the coil 122. Advantageously, blood can flow through the system 100 at this point, thereby maintaining relatively normal heart function during the procedure. Once the device 500 is released, the device 500 and system 100 will resemble FIG. 10. FIG. 10 shows the prosthetic valve 500 separated from the delivery system 100, with the delivery system 100 still extending through the lumen of the prosthetic valve 500.

Figure 11:
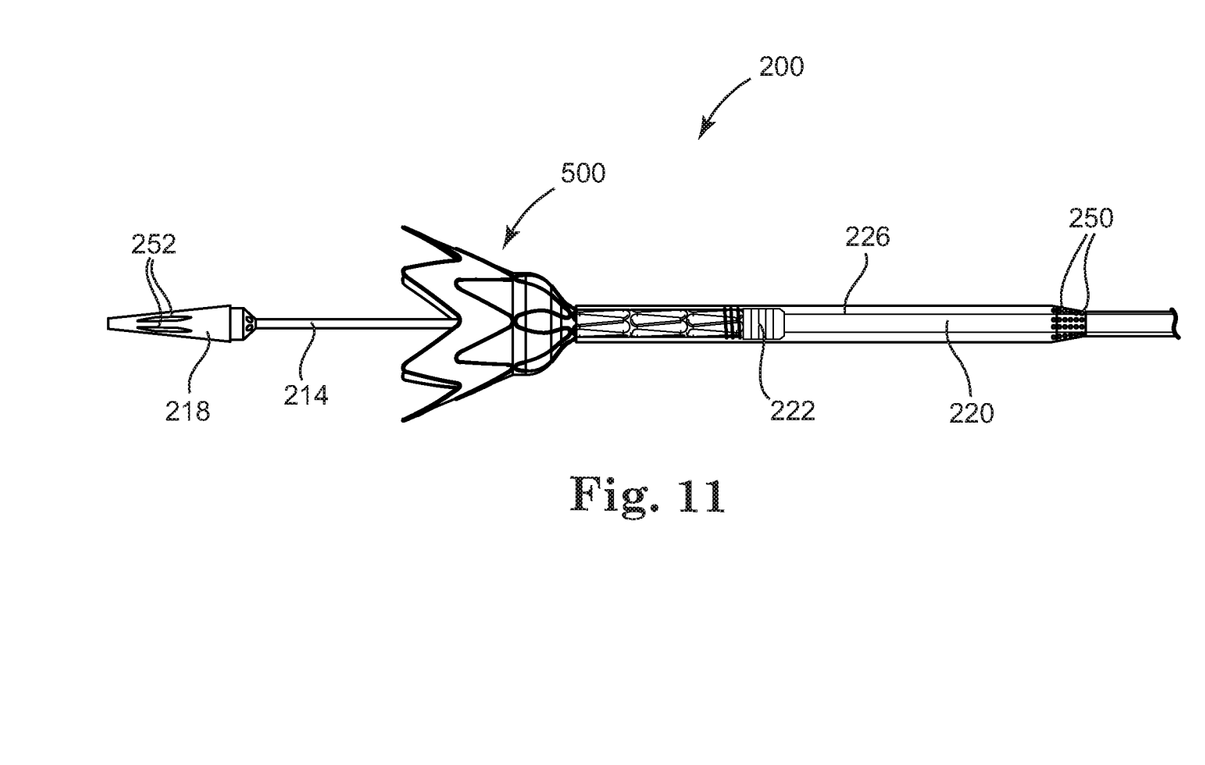
FIG. 11 illustrates an alternative embodiment of the delivery system of the present invention to the embodiment shown in FIGS. 1-10, shown with the prosthetic valve partially expanded, which incorporates dye injection into the system and allows for purging of the system.

Another embodiment of the present invention is shown in FIG. 11, that includes two additional and alternative features of the present inventive system. A distal portion of a system 200 is shown in the figure. The components of system 100 as described above are also preferably in the embodiment shown in FIG. 11, with corresponding numbers. Additionally, the embodiment shown includes dye injection ports 250 near the distal end of the system 200, and preferably at or near the proximal end of the outer sheath 226. The dye injection ports 250 preferably comprise a plurality of apertures through the outer sheath 226 and to the interior of the system 200 such that dye introduced at the proximal end of the system 200 (not shown, but preferably delivered through an access port like 108 in system 100) travels through the system 200 and out through the dye injection ports 250. The purpose of the dye injection is to allow for proximal visual alignment of the device 500 being delivered. In particular, during delivery of an infundibular reducer device 500, as shown, a partially deployed device 500 blocks flow. The dye injection ports 250 will introduce dye into the right ventricular chamber and allow for precise alignment of the device 500 in the right ventricular outflow tract. Preferably, dye injection is used together with fluoroscopy for visualization. However, visualization may be achieved by using a procedure chosen from the group consisting of fluoroscopy, echocardiography, intravascular ultrasound, angioscopy and real-time magnetic resonance imaging, for examples. However, other similar methods of visualizing the area are also contemplated for use with the dye injection.

Additionally, FIG. 11 shows a plurality of purging vents 252 preferably located on the tapered tip 218 of the system 200. The purpose of the purging vents 252 is to allow fluids, such as saline, that is injected into the system 200 (such as by an access port like that of 108 in system 100) is able to escape the system 200. Such fluid may escape through a plurality of purging ports 252 preferably located near the distal end of system 200, rather than increase the pressure inside of system 200.

With any of the systems and methods described herein, a guide wire may be initially introduced into the desired implantation site through a suitable body lumen to properly locate the desired position for the stent. The remainder of the delivery system may then be guided along the guide wire and into the site.

In the case of a prosthetic valve 500 made using bovine jugular vein or other preserved biological tissue, such as pericardial tissue, the valve can be sterilized, stored and shipped separately in a buffered glutaraldehyde solution, and may or may not be pre-mounted on the delivery system 100 or 200. Preferably, a loading rail 400 is loaded on the prosthetic valve 500 as stored. However, it is possible that the prosthetic valve 500 can also be pre-mounted on the delivery system 100 or 200 if the system with the valve 500 mounted thereon is similarly sterilized and kept in a sterile environment. In many cases, however, an implanting physician or an assistant will perform the step of mounting the prosthetic valve 500 to the delivery system 100 or 200, as described above.

The invention has now been described with reference to several embodiments thereof. The entire disclosure of any patents, patent applications, publications and journal articles identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the invention should not be limited to the structures described herein.

What is claimed is:

1. A method of loading a device onto a delivery system, the method comprising the steps of:
    extending an inner catheter through a center lumen of a holding catheter such that a distal end of the inner catheter is distal of a distal end of the holding catheter, wherein both the inner catheter and holding catheter are disposed within a center lumen of an outer sheath;
    threading a plurality of attachment members of a self-expanding device onto a loading rail, the self-expanding device including a proximal end, a distal end, and a central lumen, the plurality of attachment members located at or near the proximal end, the loading rail including two free ends;
    connecting one of the two free ends of the loading rail to a coil on the holding catheter, the coil being disposed on a distal end of the holding catheter;
    advancing the plurality of attachment members along the loading rail and onto the coil such that the coil extends through openings of the attachment members, wherein the advancing procedure partially collapses the device;
    removing the loading rail from the coil after all of the attachment members are transferred to the coil;
    collapsing the device in the outer sheath by sliding the outer sheath over the self-expanding device; and
    enclosing the collapsed device by retracting the inner catheter proximally and pulling the distal tapered end into the distal end of the outer sheath.

2. The method of claim 1, wherein the plurality of attachment members comprise loops.

3. The method of claim 1, wherein the device is a prosthetic valve further comprising a replacement valve that is attached to the device within the central lumen.

4. A method of delivering a self-expandable device to a desired anatomic site, the method comprising the steps of:
advancing a delivery system intraluminally toward a desired anatomic site, the delivery system comprising:
a self-expandable device having a proximal end and a distal end and a central lumen there through, and a plurality of attachment members at the proximal end, each of the plurality of attachment members having an opening;
an elongated inner catheter having a proximal end and a tapered, distal end for insertion into a body lumen;
an elongated holding catheter having a proximal end and a distal end and a center lumen that slidably maintains the inner catheter passing there through, and a coil on the distal end of the holding catheter, the coil being attached to the plurality of attachment members on the device by the coil extending through the openings in the plurality of attachment members; and
an elongated outer sheath having a proximal and a distal end and a center lumen passing there through slidably and rotatably maintaining the holding catheter and the inner catheter, and holding and enclosing the self-expandable device in a collapsed configuration;
upon reaching the anatomic site, retracting the outer sheath to allow the self-expandable device to partially expand;
rotating the holding catheter in order to release the attachment members of the device from the coil and allowing the device to expand, thereby releasing the device from the delivery system; and
removing the delivery system from the anatomic site.

5. The method of claim 4, wherein the device further comprises a replacement valve connected to the device in the central lumen of the device.

6. The method of claim 5, wherein the plurality of attachment members comprise loops.

7. The method of claim 4, wherein the delivery system further comprises dye injection ports through which dye may flow from the system to the anatomic site, and further comprising the step of delivering dye through the dye injection ports.

8. The method of claim 7, wherein the dye is delivered under visualization.

9. The method of claim 8, wherein visualization is achieved by using a procedure chosen from the group consisting of fluoroscopy, echocardiography, intravascular ultrasound, angioscopy and real-time magnetic resonance imaging.

* * * * *